US009786054B2

(12) United States Patent
Taguchi et al.

(10) Patent No.: US 9,786,054 B2
(45) Date of Patent: Oct. 10, 2017

(54) MEDICAL IMAGE PROCESSING DEVICE, TREATMENT SYSTEM AND MEDICAL IMAGE PROCESSING METHOD

(71) Applicant: KABUSHIKI KAISHA TOSHIBA, Tokyo (JP)

(72) Inventors: Yasunori Taguchi, Kanagawa (JP); Takeshi Mita, Kanagawa (JP); Ryusuke Hirai, Tokyo (JP); Kyoka Sugiura, Kanagawa (JP); Tomoyuki Takeguchi, Kanagawa (JP); Yukinobu Sakata, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 514 days.

(21) Appl. No.: 14/478,577

(22) Filed: Sep. 5, 2014

(65) Prior Publication Data

US 2015/0094516 A1 Apr. 2, 2015

(30) Foreign Application Priority Data

Sep. 30, 2013 (JP) ................................ 2013-204583

(51) Int. Cl.
*G06T 7/00* (2017.01)
*A61N 5/10* (2006.01)
*G06T 7/73* (2017.01)

(52) U.S. Cl.
CPC .............. *G06T 7/0044* (2013.01); *A61N 5/10* (2013.01); *A61N 5/103* (2013.01); *A61N 5/1048* (2013.01);
(Continued)

(58) Field of Classification Search
CPC .... A61B 6/00; A61B 6/02; A61B 6/12; A61B 6/52; A61B 6/54; A61B 5/00; G06T 7/74;
(Continued)

(56) References Cited

U.S. PATENT DOCUMENTS 6,307,914 B1 10/2001 Kunieda et al.
2005/0059887 A1 3/2005 Mostafavi et al.
(Continued)

FOREIGN PATENT DOCUMENTS

JP 2000-167072 6/2000
JP 3053389 6/2000
(Continued)

OTHER PUBLICATIONS

English-language machine translation of JP2003-339666.
English-language machine translation of JP2007-275346.

*Primary Examiner* — Peter Luong
(74) *Attorney, Agent, or Firm* — Nixon & Vanderhye, P.C.

(57) ABSTRACT

According to an embodiment, a medical image processing device includes a processor, and a memory. The memory that stores processor-executable instructions that, when executed by the processor, cause the processor to execute acquiring a first perspective image of a subject viewed in a first direction; setting a first region and a second region on the first perspective image, the first region including a first group of pixels around a target pixel, the second region including a second group of pixels, the second group including a pixel not included in the first group; calculating a likelihood of the target pixel, wherein the likelihood increases as a difference between pixel values included in the first group decreases and a difference between pixel values of the first group and the second group increases; and detecting a position of an object in the subject based on the likelihood.

20 Claims, 7 Drawing Sheets

(52) U.S. Cl.
CPC .............. *A61N 5/1049* (2013.01); *G06T 7/74* (2017.01); *A61N 2005/1061* (2013.01); *G06T 2207/10081* (2013.01); *G06T 2207/30096* (2013.01)

(58) Field of Classification Search
CPC G06T 2207/10081; G06T 2207/30096; A61N 5/1049; A61N 2005/1061; A61N 5/103; A61N 5/1048; A61N 5/10
See application file for complete search history.

(56) References Cited

U.S. PATENT DOCUMENTS

| | | | |
|---|---|---|---|
| 2007/0019852 | A1 | 1/2007 | Schildkraut et al. |
| 2009/0226060 | A1 | 9/2009 | Gering et al. |
| 2010/0067739 | A1 | 3/2010 | Mostafavi et al. |
| 2015/0065779 | A1 | 3/2015 | Suzuki et al. |

FOREIGN PATENT DOCUMENTS

| | | |
|---|---|---|
| JP | 2003-339666 | 12/2003 |
| JP | 2007-275346 | 10/2007 |
| JP | 2012-508035 | 4/2012 |
| JP | 2013-138883 | 7/2013 |
| JP | 2013-176458 | 9/2013 |
| JP | 2014-173943 | 9/2014 |

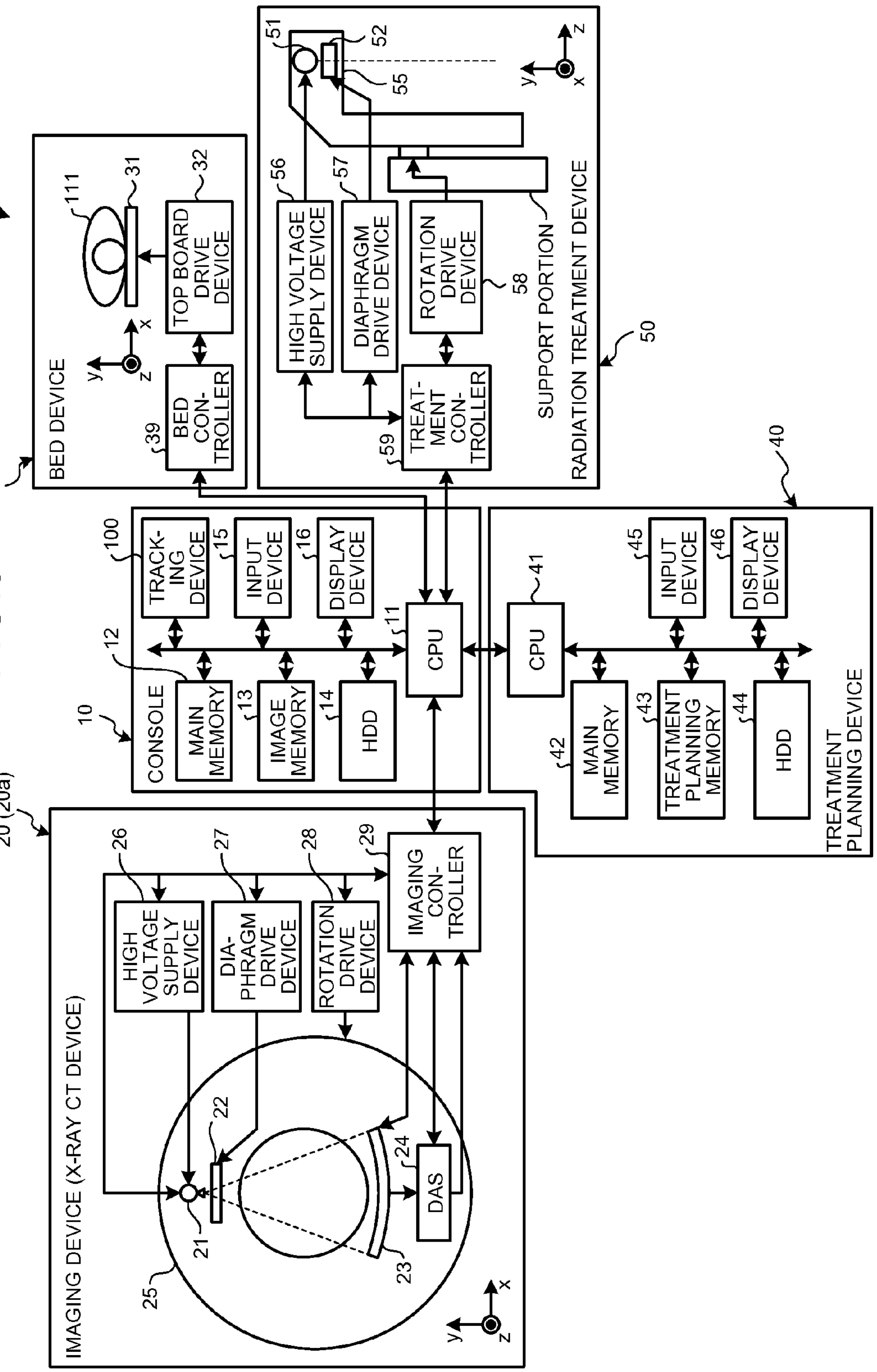
FIG.9
1
BED DEVICE
30
BED CON-TROLLER
39
TOP BOARD DRIVE DEVICE
32
31
111
RADIATION TREATMENT DEVICE
50
TREAT-MENT CON-TROLLER
59
HIGH VOLTAGE SUPPLY DEVICE
56
DIAPHRAGM DRIVE DEVICE
57
ROTATION DRIVE DEVICE
58
SUPPORT PORTION
51
52
55
CONSOLE
10
MAIN MEMORY
12
IMAGE MEMORY
13
HDD
14
CPU
11
TRACK-ING DEVICE
100
INPUT DEVICE
15
DISPLAY DEVICE
16
TREATMENT PLANNING DEVICE
40
CPU
41
MAIN MEMORY
42
TREATMENT PLANNING MEMORY
43
HDD
44
INPUT DEVICE
45
DISPLAY DEVICE
46
IMAGING DEVICE (X-RAY CT DEVICE)
20 (20a)
HIGH VOLTAGE SUPPLY DEVICE
26
DIA-PHRAGM DRIVE DEVICE
27
ROTATION DRIVE DEVICE
28
IMAGING CON-TROLLER
29
DAS
21
22
23
24
25
x
y
z

MEDICAL IMAGE PROCESSING DEVICE, TREATMENT SYSTEM AND MEDICAL IMAGE PROCESSING METHOD

CROSS-REFERENCE TO RELATED APPLICATION(S)

This application is based upon and claims the benefit of priority from Japanese Patent Application No. 2013-204583, filed on Sep. 30, 2013; the entire contents of which are incorporated herein by reference.

FIELD

Embodiments described herein relate generally to a medical image processing device, a treatment system and a medical image processing method.

BACKGROUND

As a radiation treatment method used in a case where a patient's affected area moves due to respirations, cardiac beats, and intestinal movements, an ambush irradiation method and a pursuing irradiation method are known.

In these irradiation methods, a patient's internal body is periodically imaged with perspective X-rays to periodically generate a perspective image containing an image of a patient's affected area or a marker indwelled around the affected area. Then, matching with a template is performed to track the affected area or the marker, and the affected area is irradiated with treatment beams. The template is registered, by users such as medical doctors and radiation technologists, in a perspective image for preparing a template. The perspective image for preparing a template is generated through previous imaging of the patient's internal body with perspective X-rays during, for example, treatment planning.

Alternatively, background differencing technique is performed on a perspective image that is periodically imaged during treatment to track a marker, and then, an affected area is irradiated with treatment beams.

In the method where a user registers the image of an affected area or a marker in a perspective image for preparing a template to the template, like the known techniques described above, for registering the template, a subject needs to be irradiated with perspective radiation to generate the perspective image for preparing a template. Accordingly, the exposure dose of the subject comes to be increased.

Especially, for addressing a problem that an image of the affected area and a marker in a perspective image varies in shape depending on the position of the affected area or the marker in the subject, a plurality of template perspective images are imaged at different times to register the image of the affected area and the marker in each template perspective image to the template. In such a case, the exposure dose of the subject comes to be further increased.

Furthermore, in the method of performing background differencing technique on the perspective image imaged during treatment thereby to detect the image of the marker, irradiation with perspective radiation needs to be strengthened so as to inhibit erroneous detection of noises contained in the perspective image. Accordingly, the exposure dose of the subject comes to be increased. It is noted that the affected area itself is difficult to be detected by the background differencing technique.

BRIEF DESCRIPTION OF THE DRAWINGS

FIG. 9 is a block diagram illustrating a hardware configuration example of a treatment system according to the embodiment and modifications described herein.

DETAILED DESCRIPTION

According to an embodiment, a medical image processing device includes a processor, and a memory. The memory that stores processor-executable instructions that, when executed by the processor, cause the processor to execute acquiring a first perspective image of a subject viewed in a first direction; setting a first region and a second region on the first perspective image, the first region including a first group of pixels around a target pixel, the second region including a second group of pixels, the second group including a pixel not included in the first group; calculating a likelihood of the target pixel, wherein the likelihood increases as a difference between pixel values included in the first group decreases and a difference between pixel values of the first group and the second group increases; and detecting a position of an object in the subject based on the likelihood.

An embodiment is described in detail below with reference to accompanying drawings.

Figure 1:
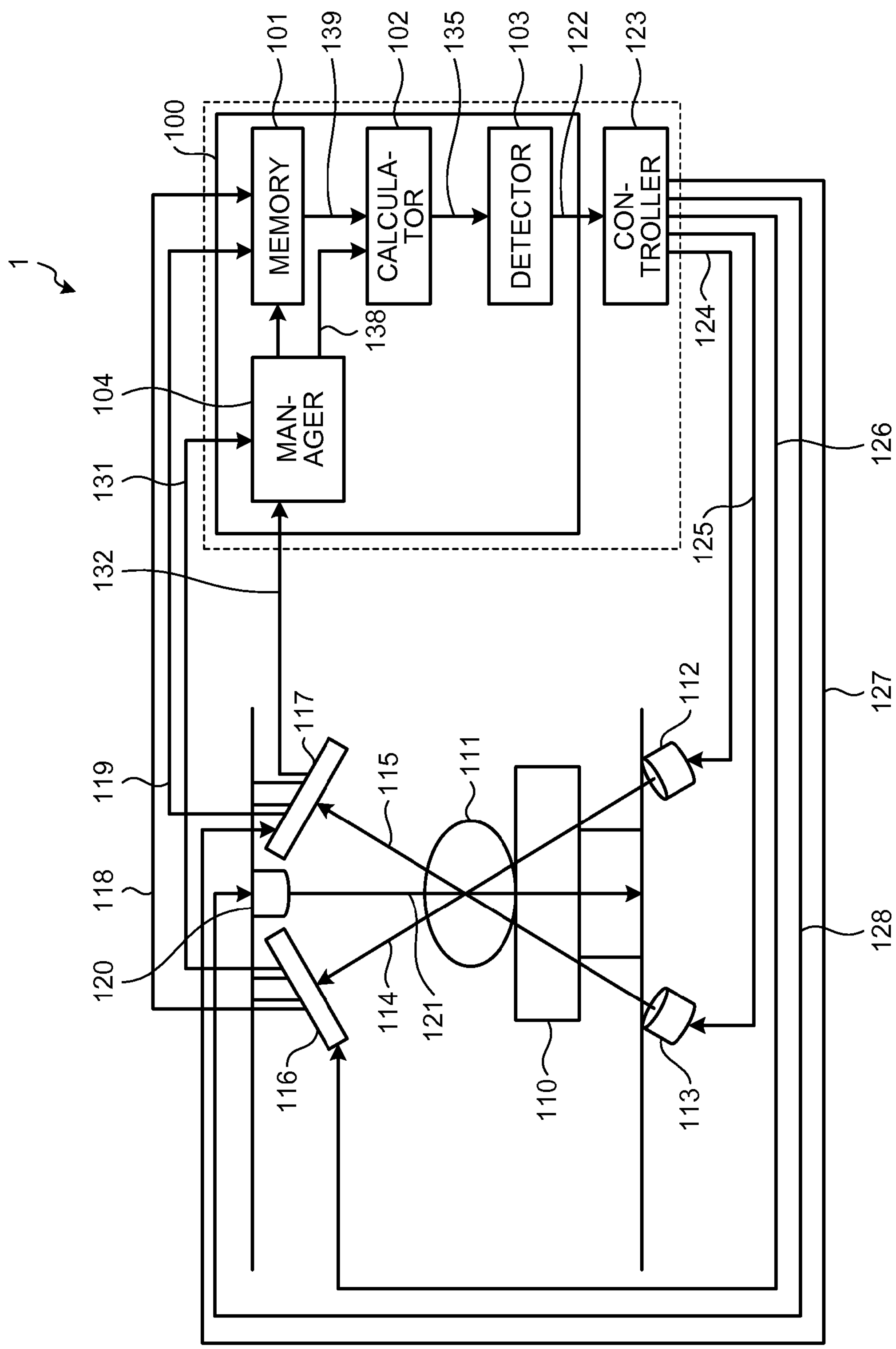
FIG. 1 is a diagram illustrating a configuration example of a treatment system according to the embodiment.

FIG. 1 is a diagram illustrating an example of a configuration of a treatment system 1 according to the embodiment. As illustrated in FIG. 1, the treatment system 1 includes a bed 110, first irradiation units 112 and 113, radiation detectors 116 and 117 (an example of a first detector), a tracking device 100 (an example of a medical image processing device), a controller 123, and a second irradiation unit 120.

In the treatment system 1 according to the embodiment, an object inside a subject 111 lying on the bed 110 moves three-dimensionally due to respirations, cardiac beats, and i intestinal movements of the subject 111. For this reason, the object is tracked using the tracking device 100. Based on the tracked object, radiation treatment is performed to an affected area of the subject 111.

Although a patient is assumed as the subject 111 in the embodiment, no limitation is made thereto. The object may be an affected area in the body of the subject 111, or a marker indwelled around the affected area. The marker is not limited as long as it is made of material (for example, gold or platinum) which is unlikely to allow radiations 114 and 115 emitted from the first irradiation units 112 and 113 to transmit through. For example, the marker may have a shape of a ball or a cylinder with a diameter of approximately 2 mm. Here, the radiation treatment includes treatment with X-rays, γ-rays, electron beams, proton beams, neutron beams, and heavy particle beams.

Although an example of using the tracking device 100 in the radiation treatment is described in the embodiment, the application of the tracking device 100 is not limited thereto. For example, the tracking device 100 can be employed for tracking the position of a catheter or a stent graft in a catheter test or a stent graft treatment. The tracking device 100 can also be employed for detecting a marker embedded in a calibration phantom during calibration for calculating a projection matrix of an imaging system in the radiation treatment.

The first irradiation units 112 and 113 respectively irradiate the subject 111 with the radiations 114 and 115. Although the first irradiation units 112 and 113 are assumed to be movable in the embodiment, no limitation is made thereto, and the first irradiation units 112 and 113 may be of a fixed-type. Although the number of first irradiation units is assumed to be two in the embodiment, it is not limited thereto, and may be one or not less than three.

The radiations 114 and 115 are used for perspectively seeing the inside of the subject 111, and may be, but not limited to, for example, X-rays.

The radiation detector 116 detects the radiation 114 having passed through the subject 111, generates a perspective image 118 of the inside of the subject 111, and outputs the generated image together with a timing signal 131 to the tracking device 100. The radiation detector 117 detects the radiation 115 having passed through the subject 111, generates a perspective image 119 of the inside of the subject 111, and outputs the generated image together with a timing signal 132 to the tracking device 100. Here, the perspective direction of the inside of the subject 111 differs between the perspective image 118 and the perspective image 119.

The radiation detectors 116 and 117 may be, for example, a combination of an image intensifier and a camera, a combination of a color image intensifier and a camera, or a flat panel detector. Although the radiation detectors 116 and 117 are assumed to be movable in the embodiment, no limitation is made thereto, and the radiation detectors 116 and 117 may be of a fixed-type. Although the number of radiation detectors is assumed to be two in the embodiment, it is not limited thereto, and may be any as long as it is the same as the number of first irradiation units.

The tracking device 100 tracks the object in the subject 111, and includes a memory 101 (an example of a storage unit), a calculator 102, a detector 103 (an example of a second detector), and a manager 104. The tracking device 100 can be implemented by, for example, a controller provided with an FPGA (Field Programmable Gate Array), a CPU (Central Processing Unit), a RAM (Random Access Memory), a ROM (Read Only Memory) and the like.

To the memory 101, the perspective image 118 is written from the radiation detector 116 at a timing when the timing signal 131 is notified to the manager 104; and the perspective image 119 is written from the radiation detector 117 at a timing when the timing signal 132 is notified to the manager 104.

To the manager 104, the timing signal 131 and the timing signal 132 are sent. The timing signal 131 notifies of a timing when the radiation detector 116 writes the perspective image 118 to the memory 101 from the radiation detector 116, and the timing signal 132 notifies of a timing when the radiation detector 117 writes the perspective image 119 to the memory 101 from the radiation detector 117.

The manager 104 manages the writing timing for each of the perspective images 118 and 119 to the memory 101, based on the timing signals 131 and 132. The manager 104 also manages an address in a storage region of the memory 101. The manager 104 also sends a timing signal 138 to the calculator 102 in order to manage a timing when information 139 is sent from the memory 101 to the calculator 102. The information 139 is the perspective images 118 and 119.

The calculator 102 acquires the information 139 from the memory 101, based on the timing signal 138. The information 139 is, as described above, the perspective images 118 and 119. The calculator 102 sets, for each target pixel, a first region and a second region to the perspective image. The first region contains two or more first pixels around the target pixel, and the second region contains one or more second pixels which are different from the two or more first pixels.

The first region desirably has a shape depending on the shape of the object. Specifically, the first region has a shape of the image of the object appearing on the perspective image. For example, when the object has a shape of a ball, the image of the object appearing on the perspective image has a shape of a circle. Therefore, the first region has a shape of a circle.

In the embodiment, the calculator 102 acquires object information regarding the shape and size of the object, and a projection matrix that is used to project three-dimensional coordinates onto the perspective image; calculates the shape and size of the image of the object appearing on the perspective image using the acquired object information and projection matrix; and sets the first region with the calculated shape and size of the image. The calculator 102 can determine the shape or type of the object, based on, for example, information specifying the mode previously input by a user.

For example, in a case where the object is the affected area of the subject 111, the shape and size of the affected area can be identified from a CT image photographed at treatment planning or a CT image photographed at diagnosis prior to the treatment planning. In this case, the CT image includes a three-dimensional profile of the affected area input by a user such as a medical doctor. The treatment planning is a plan for calculating where and how much treatment beams are emitted.

For this reason, when the object is the affected area, the calculator 102 may acquire the CT image from a treatment planning device (not illustrated in FIG. 1) while acquiring the projection matrix of the perspective image from the controller 123 described later; calculate the shape and size of the image of the affected area appearing on the perspective image using the acquired CT image and projection matrix; and set the first region with the calculated shape and size of the image.

Furthermore, for example, when the object is a marker indwelled around the affected area of the subject 111, the shape and size of the marker is already known. Therefore, a user such as a medical doctor or a radiation technologist may input the shape and size of the marker from an input device (not illustrated in FIG. 1).

For this reason, when the object is a marker, the calculator 102 may acquire the shape and size of the marker from an input device while acquiring the projection matrix of the perspective image from the controller 123 described later; calculate the shape and size of the image of the marker appearing on the perspective image using the acquired shape and size of the marker and projection matrix; and set the first region with the calculated shape and size of the image.

It is noted that, even when the object is a marker, the calculator 102 may calculate the shape and size of the image of the marker appearing on the perspective image using the CT image and the like, and set the first region with the calculated shape and size of the image, in a similar manner to the case where the object is the affected area.

When the image of the object becomes dominant with respect to the first region, the calculator 102 may set, as the second region, a region where the image of the object does not become dominant, such as the region around the first region, that is a region where anything other than the image of the object becomes dominant. Although the first region and the second region are preferably adjacent to each other, no limitation is made thereto. The first region and the second region may be separated from each other; or the first region and the second region may also be overlapped to each other.

Then, the calculator 102 calculates a likelihood for each target pixel. The likelihood is calculated so that the value thereof becomes larger when pixel values of the two or more first pixels constituting the first region are closer to each other, and a difference between the pixel values of two or more first pixels and the pixel values of one or more second pixels constituting the second region is larger. The likelihood may be, but not limited to, for example, a correlation ratio between the pixel values of two or more first pixels and the pixel values of one or more second pixels.

When the shape of the image of the object appearing on the perspective image varies depending on the direction of perspectively seeing the object, the calculator 102 may set a plurality of the first regions and the second regions for each target pixel according to the shape of the image of a possible object, and calculate the likelihood for each set of the first region and the second region so that the likelihood having the largest value is determined as the likelihood for the target pixel.

Furthermore, when the shape of the image of the object appearing on the perspective image varies depending on the direction of perspectively seeing the object, the calculator 102 may set the region which becomes dominant in any image of the object as being the first region.

In the embodiment, the calculator 102 sets the first region and the second region for each target pixel in each of the perspective images 118 and 119, calculates a likelihood 135, and outputs the calculated likelihood 135 to the detector 103. Furthermore, in the embodiment, each pixel in each of the perspective images 118 and 119 becomes a target pixel. That is, in the embodiment, the calculator 102 calculates the likelihood 135 with respect to each pixel in each of the perspective images 118 and 119, and outputs the calculated likelihood 135 to the detector 103.

Figure 2:
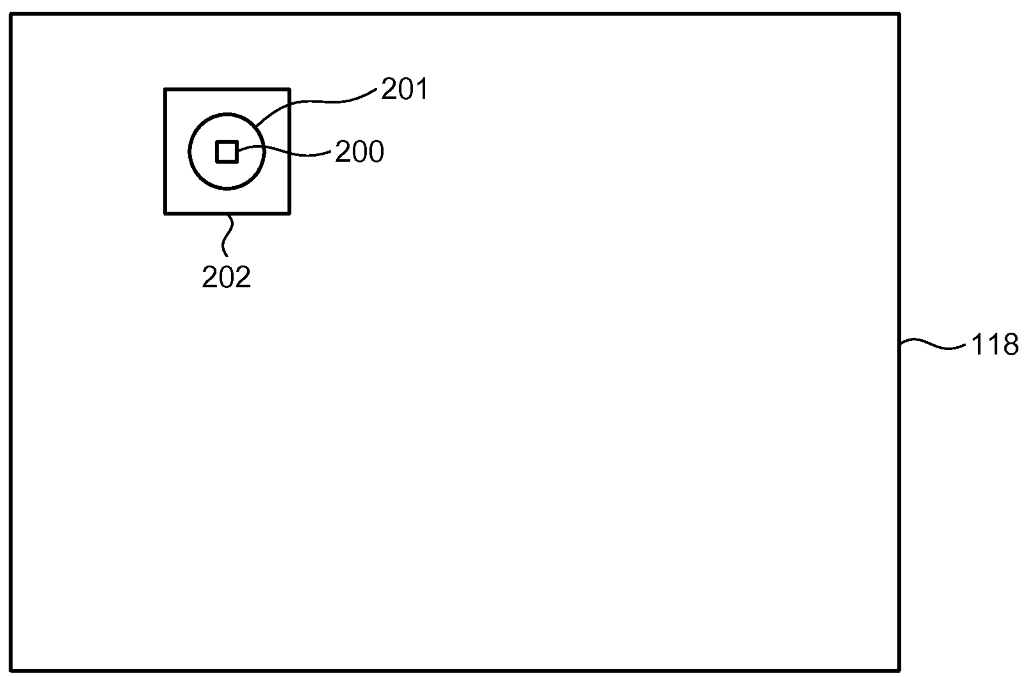
FIG. 2 is an illustrative diagram of a likelihood calculation method example according to the embodiment.

FIG. 2 is an illustrative diagram of an example of a likelihood calculation method according to the embodiment. In the example illustrated in FIG. 2, the likelihood calculation method is described using a target pixel 200 of the perspective image 118 as an example. For other target pixels of the perspective image 118 or the target pixels of the perspective image 119, a similar likelihood calculation method is used. In the example illustrated in FIG. 2, an object has a shape of a ball.

In the example illustrated in FIG. 2, the object has a shape of a ball, and an image of the object appearing on the perspective image 118 has a shape of a circle. Therefore, the calculator 102 sets, for the perspective image 118, a first region 201 having a shape of a circle around the target pixel 200, and a second region 202 including the inside of a rectangle containing the first region 201 therein and the outside of the first region 201. In this case, the pixels constituting the first region 201 are the first pixels; and the pixels constituting the second region 202 are the second pixels.

Then, in a case of the example illustrated in FIG. 2, the likelihood of the target pixel 200 is represented by $\sigma_b^2/\sigma_t^2$. Here, $\sigma_t$ represents a standard deviation of the values for all pixels contained in a union of the first region 201 and the second region 202 (a union of the first pixels and the second pixels), and $\sigma_b$ is represented by mathematical formula (1).

$$\sigma_b = \sqrt{\frac{n_1(m_1 - m_t)^2 + n_2(m_2 - m_t)^2}{n_t}} \tag{1}$$

Here, $n_1$ represents the number of pixels for the first pixels constituting the first region 201; $n_2$ represents the number of pixels for the second pixels constituting the second region 202; and $n_t$ represents the number of pixels for the pixels contained in a union of the first region 201 and the second region 202 (a union of the first pixels and the second pixels). Furthermore, $m_1$ represents an average value of the pixel values for the first pixels constituting the first region 201; $m_2$ represents an average value of the pixel values for the second pixels constituting the second region 202; and $m_t$ represents an average value of the pixel values for the pixels contained in a union of the first region 201 and the second region 202 (a union of the first pixels and the second pixels).

In brief, $\sigma_b^2/\sigma_t^2$ comes to be a correlation ratio between a set of the pixel values for the first pixels constituting the first region 201 and a set of the pixel values for the second pixels constituting the second region 202.

Here, $\sigma_b^2/\sigma_t^2$ has a value of 0 to 1, and becomes larger (the value becomes closer to 1) when the pixel values for the first pixels constituting the first region 201 are closer to each other, and a difference between the pixel values for the first pixels constituting the first region 201 and the pixel values for the second pixels constituting the second region 202 is larger.

Accordingly, when the image of the object becomes dominant with respect to the first region 201, and the image other than the object becomes dominant with respect to the second region 202, $\sigma_b^2/\sigma_t^2$ has a larger value. On the other hand, when the image having the same composition is dominant in both the first region 201 and the second region 202, $\sigma_b^2/\sigma_t^2$ has a smaller value (the value is closer to 0).

Especially, in the embodiment, the first region is set by the shape and size of the image (a circle in the example illustrated in FIG. 2) of the object appearing on the perspective image. Therefore, the value of $\sigma_b^2/\sigma_t^2$ becomes significantly larger when the image of the object conforms to the first region 201 compared with when the image of the object does not conform to the first region 201.

Here, definition of $\sigma_w^2=\sigma_t^2+\sigma_b^2$ leads to establishment of mathematical formula (2). Therefore, $\sigma_b^2/\sigma_t^2$ can be calculated also by $1/((\sigma_w^2/\sigma_b^2)+1)$. Since the denominator $\sigma_t^2$ of $\sigma_b^2/\sigma_t^2$ can be 0, $\sigma_b^2/(\sigma_t^2+\epsilon)$ may be defined as the likelihood of the target pixel 200. In this case, $\epsilon$ is a positive small value. Since the denominator $\sigma_b^2$ of $\sigma_w^2/\sigma_b^2$ can be 0, $1/((\sigma_w^2/(\sigma_b^2+\epsilon))+1)$ may be defined as the likelihood of the target pixel 200.

$$\frac{\sigma_b^2}{\sigma_t^2} = \frac{\sigma_b^2}{\sigma_w^2 + \sigma_b^2} = \frac{1}{\frac{\sigma_w^2}{\sigma_b^2} + 1} \quad (2)$$

Although in the example illustrated in FIG. 2, the likelihood of the target pixel 200 ($\sigma_b^2/\sigma_t^2$) is a correlation ratio between a union of the pixel values for the first pixels constituting the first region 201 and a union of the pixel values for the second pixels constituting the second region 202, the likelihood of the target pixel 200 may not be the correlation ratio, as long as the value of the likelihood becomes larger when the pixel values for the first pixels are closer to each other, and a difference between the pixel values for the first pixels and the pixel values for the second pixels is larger.

For example, the likelihood may have a larger value when: the pixel values for the first pixels constituting the first region 201 are closer to each other; the pixel values for the first pixels indicate low radiation transmittance; and a difference between the pixel values for the first pixels and the pixel values for the second pixels is larger.

However, the perspective image may have a reversed density in some cases. Accordingly, low radiation transmittance may cause the value of the pixels to decrease in some cases and to increase in other cases. Therefore, the likelihood whose value is larger under low radiation transmittance needs to be designed in accordance with the specification of the perspective image. For this reason, in a case of a perspective image having a smaller pixel value under low radiation transmittance, the likelihood when $m_1$ is less than a predetermined threshold may be defined as 0 or a positive small value $\epsilon$, and the likelihood when $m_1$ is not less than a predetermined threshold may be defined as $\sigma_b^2/\sigma_t^2$.

The detector 103 detects the position of the object in the subject 111, based on the likelihood calculated by the calculator 102 for each target pixel in the perspective image. Specifically, the detector 103 detects that the image of the object is located in the target pixel having a likelihood whose value size satisfies a predetermined condition.

In the embodiment, the detector 103 acquires a projection matrix that is used to project three-dimensional coordinates on the perspective image 118 and a projection matrix that is used to project three-dimensional coordinates on the perspective image 119, and detects the target pixel having a likelihood whose value size satisfies a predetermined condition among the likelihoods 135 of the target pixels for each of the perspective images 118 and 119.

Accordingly, the detector 103 detects that the image of the object is located in the detected target pixel for each of the perspective images 118 and 119. The projection matrix for each of the perspective images 118 and 119 can be acquired from the controller 123 described later. The predetermined condition can be, for example, the largest value, the value exceeding a threshold, or the value exceeding a threshold and being the largest.

Then, the detector 103 detects the three-dimensional position of the object, using the projection matrix for each of the perspective images 118 and 119 and the target pixels detected from each of the perspective images 118 and 119. For example, the detector 103 calculates the three-dimensional position of the object from the target pixels (the image of the object) detected from each of the perspective images 118 and 119 based on epipolar geometry using the projection matrix for each of the perspective images 118 and 119, and outputs position information 122, which indicates the calculated three-dimensional position, to the controller 123.

When a plurality of the objects exists in the subject 111, the detector 103 acquires, for each of the perspective images 118 and 119, region information which indicates a third region where each of the plurality of objects is expected to exist.

For example, when the third region for each object is input by a user such as a medical doctor in the above-described CT image, the detector 103 acquires, as region information, the CT image corresponding to each of the perspective images 118 and 119 from the above-described treatment planning device (not illustrated in FIG. 1).

Furthermore, for example, when the third region for each object is input to the perspective images 118 and 119 by a user such as a medical doctor and a radiation technologist, the detector 103 acquires region information by acquiring the perspective images 118 and 119 from the calculator 102.

In this case, the user may specify a point to the perspective images 118 and 119 displayed on a display device (not illustrated in FIG. 1) by mouse click or touch panel operation, so that a region around the specified point is defined as the third region. In this manner, even when the perspective images 118 and 119 are reproduced as moving images, the user can easily input the third region.

Next, the detector 103 detects a plurality of target pixels each having a likelihood whose value size satisfies a predetermined condition, among the likelihoods 135 of the target pixels, for each of the perspective images 118 and 119. The predetermined condition can be, for example, the value having an order in size falling in the number of higher-order objects, the value exceeding a threshold, or the value exceeding a threshold and having an order in size falling in the number of higher-order objects.

Next, the detector 103 detects which third region each of the plurality of target pixels detected from the perspective image 118 exists in, using the region information of the perspective image 118. At the same time, the detector 103 detects which third region each of the plurality of target pixels detected from the perspective image 119 exists in, using the region information of the perspective image 119. Thereafter, the detector 103 allows the plurality of target pixels (images for the plurality of objects) detected from each of the perspective images 118 and 119 to be corresponded to each other between the perspective images 118 and 119.

Next, the detector 103 detects the three-dimensional positions for the plurality of objects, using the projection matrix for each of the perspective images 118 and 119, and the plurality of target pixels (images for the plurality of objects) which were detected from each of the perspective images 118 and 119 and corresponded to each other between the perspective images 118 and 119.

Figure 3A:
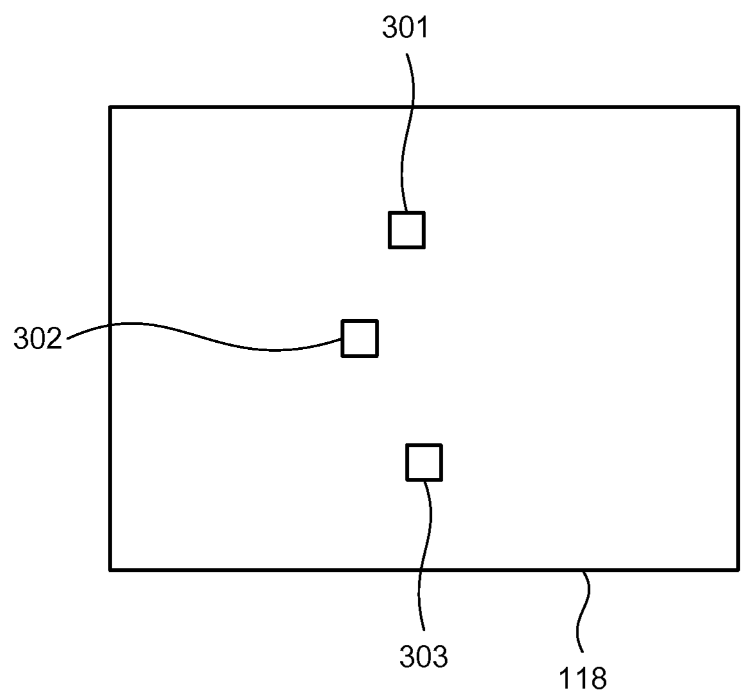
FIG. 3A is an illustrative diagram of an example of an object image correspondence method according to the embodiment.
Figure 3B:
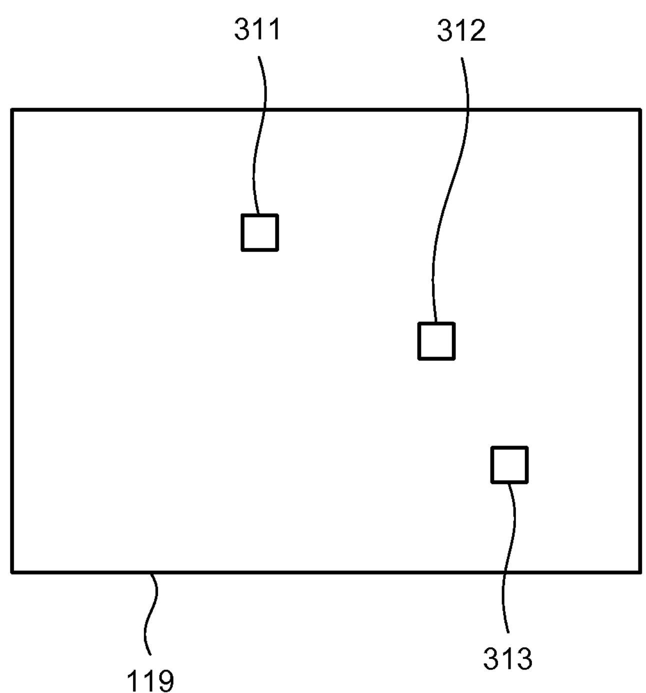
FIG. 3B is an illustrative diagram of an example of an object image correspondence method according to the embodiment.

FIG. 3A and FIG. 3B are an illustrative diagram of an example of an object image correspondence method according to the embodiment. In the example illustrated in FIG. 3A and FIG. 3B, the number of objects are three. As illustrated in FIG. 3A, in the perspective image 118, the target pixels 301, 302 and 303, in which each image of three objects are located, are detected. Furthermore, as illustrated in FIG. 3B, in the perspective image 119, the target pixels 311, 312 and 313, in which each image of three objects are located, are detected.

In this case, the detector 103 detects which third region each of the target pixels 301, 302 and 303 detected from the perspective image 118 exists in, using the region information of the perspective image 118. At the same time, the detector 103 detects which third region each of the target pixels 311, 312 and 313 detected from the perspective image 119 exists in, using the region information of the perspective image 119.

For example, the third regions of ID=1 to 3 are indicated in the region information for each of the perspective images 118 and 119. Here, the target pixel 301 exists in the third region of ID=1 in the perspective image 118; the target pixel 302 exists in the third region of ID=2 in the perspective image 118; the target pixel 303 exists in the third region of D=3 in the perspective image 118; the target pixel 311 exists in the third region of ID=1 in the perspective image 119; the target pixel 312 exists in the third region of ID=2 in the perspective image 119; and the target pixel 313 exists in the third region of ID=3 in the perspective image 119. The third regions having an identical ID in the perspective images 118 and 119 are the same region.

Therefore, the detector 103 allows the target pixel 301 and the target pixel 311, the target pixel 302 and the target pixel 312, and the target pixel 303 and the target pixel 313 to be corresponded to each other between the perspective images 118 and 119.

Thus, even when the plurality of objects exists, the images of the same object can be corresponded to each other between the perspective images 118 and 119, enabling calculation of the three-dimensional position of the object.

The controller 123 outputs a control signal 128 to the second irradiation unit 120 based on the position information 122 from the detector 103, and controls irradiation of the object (affected area) with a treatment beam 121 by the second irradiation unit 120.

The control signal 128 is a signal that controls the irradiation timing with the treatment beam 121 by the second irradiation unit 120 in a case of the ambush irradiation method, and the position information of the object (affected area) in a case of the pursuing irradiation.

The controller 123 also outputs timing signals 124, 125, 126 and 127 to the first irradiation units 112 and 113 and the radiation detectors 116 and 117 respectively, to control action timings of the first irradiation units 112 and 113 and the radiation detectors 116 and 117.

The controller 123 also controls the first irradiation units 112 and 113 and the radiation detectors 116 and 117 to perform, for example, test generation (imaging) of the perspective images 118 and 119, so as to previously generate projection matrices for the perspective images 118 and 119 and retain the generated projection matrices.

The controller 123 can be implemented by, for example, a controller provided with a CPU, a RAM, a ROM and the like. When the tracking device 100 is also implemented by a controller, the tracking device 100 and the controller 123 may be implemented by the same controller, or may be implemented by different controllers.

The second irradiation unit 120 irradiates the object (affected area) with the treatment beam 121, based on the three-dimensional position of the object detected by the detector 103. Specifically, the second irradiation unit 120 irradiates the object (affected area) with the treatment beam 121, based on the control signal 128 from the controller 123.

Although in the embodiment, the treatment beam 121 is assumed to be heavy particle beams, no limitation is made thereto, and may be X-rays, γ-rays, electron beams, proton beams, neutron beams and the like.

Figure 4:
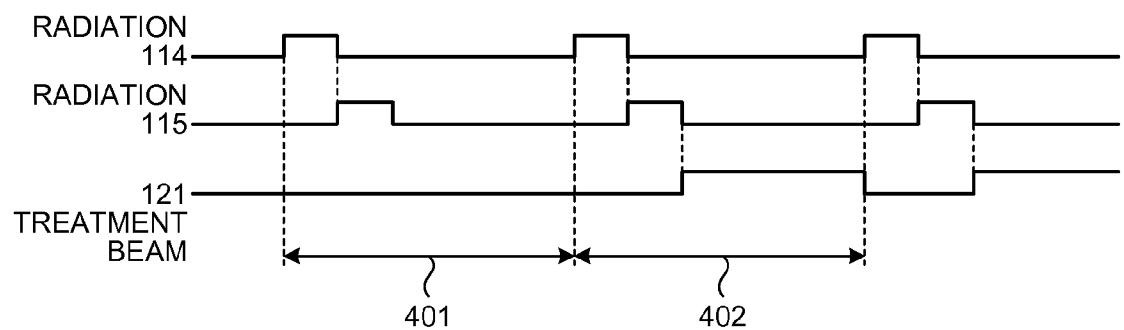
FIG. 4 is a timing chart illustrating an irradiation timing example of radiation and treatment beams according to the embodiment.

FIG. 4 is a timing chart illustrating an example of the irradiation timing of the radiations 114 and 115 and the treatment beams 121 according to the embodiment.

In the embodiment, concurrent irradiation with the radiations 114 and 115 and the treatment beam 121 causes the perspective images 118 and 119 to become noisy under influence of radiation scattering. For this reason, the controller 123 controls the first irradiation units 112 and 113 and the second irradiation unit 120 so that each of the radiations 114 and 115 and the treatment beam 121 is independently emitted.

For example, when irradiation is performed from each direction 30 times per one second, the controller 123 controls, as illustrated in FIG. 4, the first irradiation units 112 and 113 and the second irradiation unit 120 so that the radiations 114 and 115 and the treatment beam 121 are independently emitted every 1/30 seconds. Times 401 and 402 each indicate 1/30 seconds.

Figure 5:
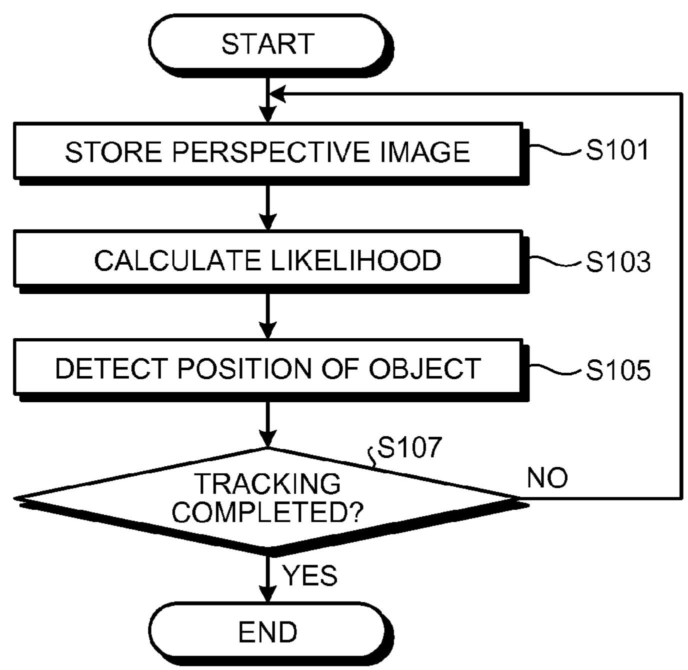
FIG. 5 is a flowchart illustrating a processing example of a tracking device according to the embodiment.

FIG. 5 is a flowchart illustrating an example of processing by the tracking device 100 according to the embodiment.

First, to the memory 101, the perspective image 118 is written from the radiation detector 116; and the perspective image 119 is written from the radiation detector 117 (step S101).

Subsequently, the calculator 102 reads the information 139 (the perspective images 118 and 119) from the memory 101, sets the first region and the second region for each target pixel in each of the perspective images 118 and 119, and calculates the likelihood 135 (step S103).

Subsequently, the detector 103 detects the target pixel having a likelihood whose value size satisfies a predetermined condition for each of the perspective images 118 and 119, and detects the three-dimensional position of the object, using the projection matrix for each of the perspective images 118 and 119 and the target pixel detected from each of the perspective images 118 and 119 (step S105).

When tracking of the three-dimensional position of the object is continued (No in step S107), the process returns to step S101, and when tracking of the three-dimensional position of the object is terminated (Yes in step S107), the process is terminated.

As described above, according to the embodiment, the position of the object can be detected from the perspective image generated during treatment. For this reason, previous fluoroscopy with radiation for detecting the position of the object such as registration of the template becomes unnecessary, enabling reduction in the exposure dose of the subject with perspective radiation.

Furthermore, when the correlation ratio is used as the likelihood as in the embodiment, the likelihood is robust to noises. For this reason, even lower perspective radiation strength allows for detection of the object, enabling reduction in the exposure dose of the subject by perspective radiation.

First Modification

In the above-mentioned embodiment, when the plurality of objects exists in the subject 111, the detector 103 allows for correspondence of the images for the same object between the perspective images 118 and 119 using the region information for each of the perspective images 118 and 119. In a first modification, an example of correspondence of the images for the same object between the perspective images 118 and 119 using epipolar geometry is described.

In this case, the detector 103 may allow the plurality of target pixels (images for the plurality of objects) detected from each of the perspective images 118 and 119 to be corresponded to each other between the perspective images 118 and 119, based on epipolar geometry using the projection matrix for each of the perspective images 118 and 119.

Figure 6A:
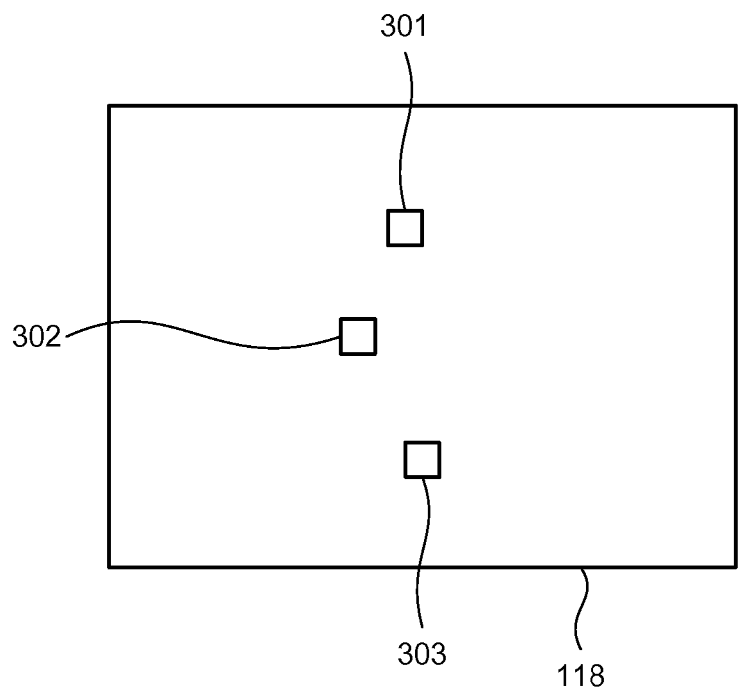
FIG. 6A is an illustrative diagram of an example of an object image correspondence method according to a first modification.
Figure 6B:
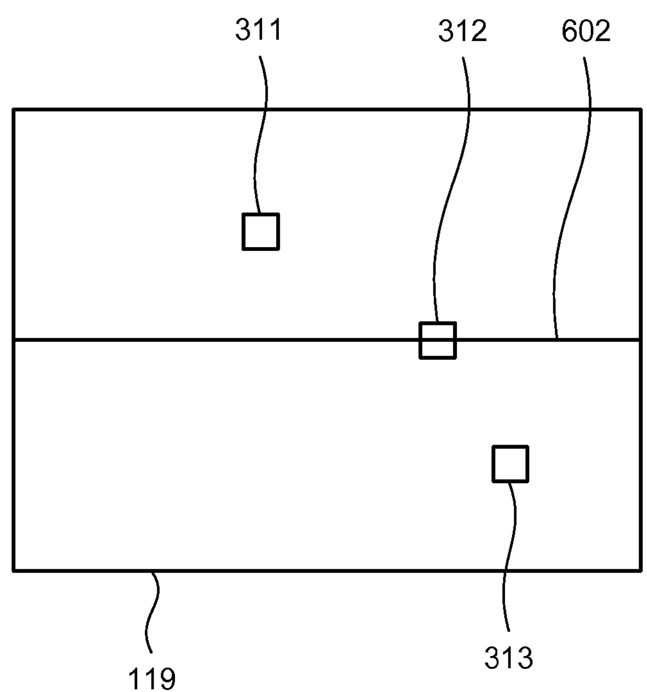
FIG. 6B is an illustrative diagram of an example of an object image correspondence method according to the first modification.

FIG. 6A and FIG. 6B are an illustrative diagram of an example of the object image correspondence method according to the first modification. In the example illustrated in FIG. 6A and FIG. 6B, the number of objects are three. As illustrated in FIG. 6A, in the perspective image 118, the target pixels 301, 302 and 303, where each of the images of the three objects is located, are detected. As illustrated in FIG. 6B, in the perspective image 119, the target pixels 311, 312 and 313, where each of the images of the three objects is located, are detected.

In the example illustrated in FIG. 6A and FIG. 6B, the correspondence method of the target pixel 302 of the perspective image 118 is described. Correspondence for each of the target pixels 301 and 303 of the perspective image 118 can be performed in a similar method.

The detector 103 calculates an epipolar line 602 of the perspective image 119 corresponding to the target pixel 302, using the target pixel 302 and the projection matrix for each of the perspective images 118 and 119. Then, the detector 103 calculates a projection length (a length of a perpendicular line) with respect to the epipolar line 602 for each of the target pixels 311, 312 and 313, and brings the target pixel 312 having the shortest projection length into correspondence with the target pixel 302.

Thus, even when the plurality of objects exists, the images of the same object can be corresponded to each other between the perspective images 118 and 119, enabling calculation of the three-dimensional position of the object.

In the example illustrated in FIG. 6A and FIG. 6B, since a difference between the minimum projection length and the second minimum projection length is large, correspondence error hardly occurs. However, when a difference between the minimum projection length and the second minimum projection length is small, correspondence error can occur. In this case, judgment on the correspondence can be postponed to the next frame.

Second Modification

In the above-mentioned embodiment, the likelihood is calculated using each pixel of the perspective image as the target pixel. In a second modification, an example of calculating the likelihood using each of the pixels constituting the third region where the image of the object is expected to exist in the perspective image is described.

In this case, the calculator 102 may acquire region information indicating the third region where the image of the object is expected to exist in the perspective image, and calculate the likelihood for each target pixel in the third region indicated by the region information. The region information may be acquired in a method similar to the above-described embodiment.

According to the second modification, the likelihood can be calculated only by pixels for a part of the perspective image, enabling reduction of the likelihood calculation time. As a result, a possibility of completing likelihood calculation by the timing when treatment beams are to be emitted can be increased. Accordingly, a state in which the completion of likelihood calculation and the irradiation with treatment beams cannot be achieved can be inhibited. Furthermore, the frequency of generation (imaging) of the perspective image can be reduced, enabling decrease in the exposure dose of the subject by perspective radiation. Furthermore, a time from generation (imaging) of the perspective image to irradiation with treatment beams can be shortened.

The higher the frame rate of the perspective image is, the more effective the method according to the second modification is.

Third Modification

In the above-mentioned embodiment, the likelihood is calculated using each pixel of the perspective image as the target pixel. In a third modification, an example is described in which once the image of the object is detected in the perspective image, a fourth region (a destination of movement of the object image) where the image of the object is expected to exist is estimated based on a predetermined motion model. Then, the likelihood is calculated using each of the pixels constituting the estimated fourth region as the target pixel.

In this case, the calculator 102 may estimate the fourth region where the image of the object is expected to exist in the perspective image, based on the predetermined motion model, and calculate the likelihood for each target pixel in the fourth region. The predetermined motion model is, for example, a uniform motion model or a uniformly accelerated motion model.

According to the third modification, the likelihood can be calculated only by pixels for a part of the perspective image, enabling reduction of the likelihood calculation time. As a result, a possibility of completing likelihood calculation by the timing when treatment beams are to be emitted can be increased. Accordingly, a state in which the completion of likelihood calculation and the irradiation with treatment beams cannot be achieved can be inhibited. Furthermore, the frequency of generation (imaging) of the perspective image can be reduced, enabling decrease in the exposure dose of the subject by perspective radiation. Also, a time from the generation (imaging) of the perspective image to the irradiation with treatment beams can be shortened.

The higher the frame rate of the perspective image is, the more effective the method according to the third modification is.

Fourth Modification

In the third modification, the likelihood is calculated in the fourth region estimated based on the predetermined motion model. In a fourth modification, an example is described in which in addition to the likelihood in the fourth region, a prior probability based on the predetermined motion model is used to detect the position of the object.

In this case, the detector 103 may set the prior probability to the fourth region. The value of the prior probability becomes larger as closer to the position to which the image of the object moves based on the predetermined motion model. Then, the detector 103 may detect the position of the object based on the likelihood and the prior probability for each target pixel. For example, the detector 103 may calculate a posterior probability that is a product of the likelihood and the prior probability for each target pixel, and detect the position of the object based on the calculated posterior probability.

Figure 7:
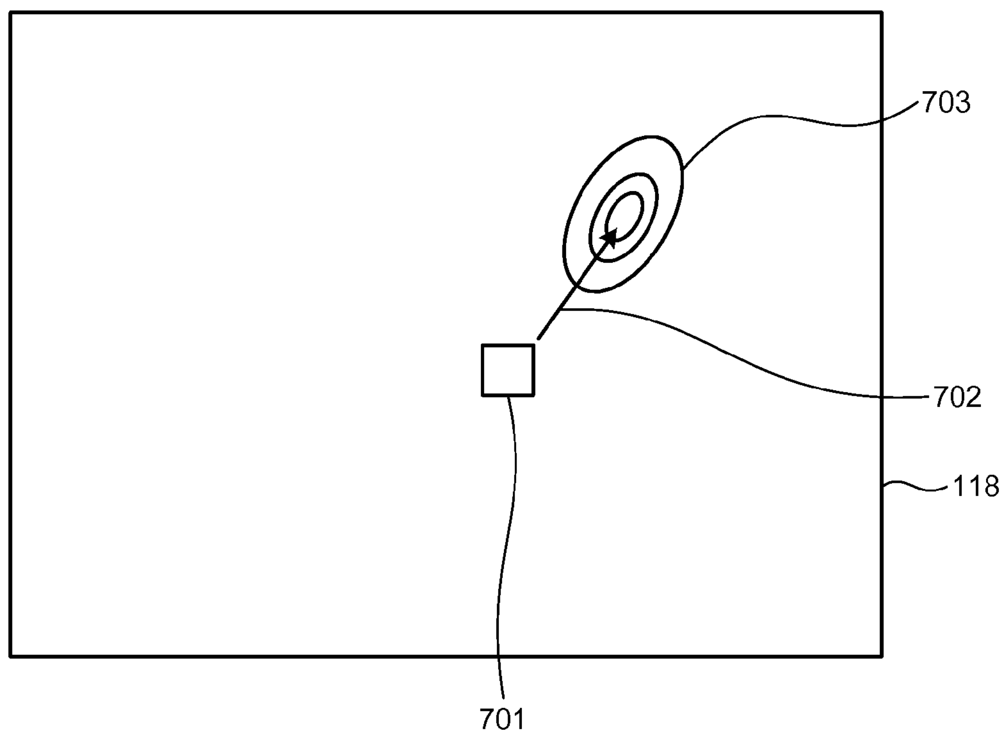
FIG. 7 is an illustrative diagram of an example of a detection method of an object position using a posterior probability according to a fourth modification.

FIG. 7 is an illustrative diagram of an example of the detection method of the position of the object using the posterior probability according to the fourth modification. In the example illustrated in FIG. 7, in a frame, a target pixel 701 of the perspective image 118 is detected as the position of the image of the object; in the next frame, the image of the object is estimated to move in the direction of an arrow 702 based on the predetermined motion model; and a prior probability distribution 703 for each of the pixels constituting the fourth region is set to the fourth region. The distribution 703 may be set by, for example, a two-dimensional normal distribution.

The distribution 703 is a distribution in which the value is largest at the position to which the image of the object is expected to move according to the predetermined motion model, and the value is smaller as the distance from the position is larger. Here, the distribution 703 may be a distribution in which even when the distance from the position is the same, the value is larger at the position along the direction of the arrow 702 than at the position in the direction vertical to the direction of the arrow 702.

When the image of the object is detected in one of the perspective images 118 and 119, the prior probability distribution to be set in the fourth region of the other may be a distribution in which: the value is largest at the position to which the image of the object is expected to move according to the predetermined motion model, and the value is smaller as the distance from the position is larger; even when the distance from the position is the same, the value is larger at the position along the direction of the arrow 702 than at the position in the direction vertical to the direction of the arrow 702; and the value is larger at the position along the epipolar line than at the position in the direction vertical to the epipolar line.

According to the fourth modification, tracking which is robust to noises of the perspective image can be achieved. As a result, since tracking is enabled even under the lowered perspective radiation dose, the exposure dose of the subject by perspective radiation can be decreased.

Fifth Modification

In the fourth modification, the position of the object is detected based on the posterior probability that is a product of the likelihood and the prior probability for each target pixel. Alternatively, using the posterior probability in the frame as the prior probability in the next frame, the posterior probability of the next frame may be calculated, to detect the position of the object based on the calculated posterior probability.

According to the fifth modification, tracking which is robust to noises of the perspective image can be achieved. As a result, since tracking is enabled even under the lowered perspective radiation dose, the exposure dose of the subject by perspective radiation can be decreased.

Sixth Modification

In the third modification, the likelihood is calculated in the fourth region estimated based on the predetermined motion model to detect the position of the object. Alternatively, a particle filter may be used to detect the position that allows the posterior probability to be maximized.

According to the sixth modification, tracking which is robust to noises of the perspective image can be achieved. As a result, since tracking is enabled even under the lowered perspective radiation dose, the exposure dose of the subject by perspective radiation can be decreased.

Seventh Modification

In the fourth modification, when the plurality of objects exists inside the subject 111, the kurtosis of the prior probability distribution 703 may be changed depending on the distance among the objects.

In this case, the calculator 102 may estimate the fourth region where the image for each of the plurality of objects is expected to exist in the perspective image, based on the predetermined motion model, and calculate the likelihood for each target pixel in each of the plurality of fourth regions.

Furthermore, the detector 103 sets the prior probability for each image of the object to the fourth region where the image is expected to exist. The value of the prior probability becomes larger as closer to the position to which the image moves based on the predetermined motion model, and has a higher kurtosis when the distance among the plurality of images is not more than a threshold. Then, the detector 103 may detect the position of the object for each fourth region, based on the likelihood and the prior probability for each target pixel.

According to the seventh modification, when the distance among the plurality of images is not more than a threshold, the estimated position based on the predetermined motion model from the past frame has priority over the likelihood based on the appearance of the perspective image of the current frame. Therefore, even when the plurality of images is crossed with each other, the risk of mistaking the image can be reduced. As a result, since the number of frames in which the image of the object cannot be tracked decreases, the frequency of the generation (imaging) of the perspective image can be reduced, enabling decrease in the exposure dose of the subject by perspective radiation.

Eighth Modification

In the seventh modification, when the distance among the plurality of images is not more than a threshold, the kurtosis of the prior probability distribution is heightened, so that the risk of mistaking the image of the object is reduced. On the other hand, in an eighth modification, an example is described in which when the distance among the images is not more than a threshold, the position of at least one of the first irradiation units 112 and 113 and the radiation detectors 116 and 117 is controlled to inhibit the distance among the object images from becoming not more than a threshold. Here, in the seventh modification, the first irradiation units 112 and 113 and the radiation detectors 116 and 117 need to be movable.

In this case, the detector 103 sets the prior probability for each image of the object to the fourth region where the image is expected to exist. The value of the prior probability becomes larger as closer to the position to which the image moves based on the predetermined motion model. Then, the detector 103 detects the position of the object for each fourth region, based on the likelihood and the prior probability for each target pixel.

Then, when the distance among the plurality of images is not more than a threshold, the detector 103 may calculate position information of at least one of the first irradiation units 112 and 113 and the radiation detectors 116 and 117 by which the perspective image is generated such that the distance among the plurality of images exceeds the threshold.

For example, the detector 103 acquires the projection matrices corresponding to several patterns among possible moving positions for each of the first irradiation units 112 and 113 and the radiation detectors 116 and 117, and calculates image coordinates for the image of each object in the perspective images 118 and 119 which are imaged in accordance with the positions of the first irradiation units 112 and 113 and the radiation detectors 116 and 117, based on the three-dimensional coordinates for each object and each projection matrix. Then, the detector 103 may extract position information of the first irradiation units 112 and 113 and the radiation detectors 116 and 117 which allows the distance among the object images to exceed a threshold (preferably, to become maximum).

Alternatively, the detector 103 may calculate the image coordinates for the image of each object in the perspective images 118 and 119 which are imaged in accordance with the positions of the first irradiation units 112 and 113 and the radiation detectors 116 and 117, from the estimated position according to the predetermined motion model in the three-dimensional coordinates for each object and each projection matrix.

The controller 123 may control the position for at least one of the first irradiation units 112 and 113 and the radiation detectors 116 and 117, based on the position information calculated by the detector 103.

According to the eighth modification, since the plurality of images comes not to be crossed with each other, the mistaking of the image does not occur. As a result, since the number of frames in which the image of the object cannot be tracked decreases, the frequency of the generation (imaging) of the perspective image can be reduced, enabling decrease in the exposure dose of the subject by perspective radiation.

Ninth Modification

In the third modification, each of the pixels constituting the fourth region estimated based on the predetermined motion model is used as the target pixel to calculate the likelihood. Alternatively, the fourth region may be further limited by an epipolar line to calculate the likelihood.

For example, when the image of the object is detected in the perspective image 118, the object image also exists on the epipolar line of the perspective image 119. Here, even when distortion of the perspective image cannot be corrected, the object image exists around the epipolar line.

For this reason, the calculator 102 may calculate the likelihood for each target pixel, around the epipolar line in the fourth region estimated in the perspective image 119.

According to the ninth modification, the likelihood can be calculated only by pixels for a part of the perspective image, enabling reduction of the likelihood calculation time. As a result, a possibility of completing likelihood calculation by the time when treatment beams are to be emitted can be increased. Accordingly, a state in which the completion of likelihood calculation and the irradiation with treatment beams cannot be achieved can be inhibited. Furthermore, the frequency of the generation (imaging) of the perspective image can be reduced, enabling decrease in the exposure dose of the subject by perspective radiation. Also, a time from the generation (imaging) of the perspective image to the irradiation with treatment beams can be shortened.

As the frame rate of the perspective image is higher, the effectiveness of the method according to the ninth modification increases.

Tenth Modification

In the above-described embodiment, after the completion of writing of the perspective image to the memory 101, the perspective image is read from the memory 101 to start calculation of the likelihood. In contrast, in a tenth modification, an example is described in which after the timing to write, to the memory, all pixels necessary for calculation of the likelihood in the target pixel in which calculation of the likelihood is to be first performed, the calculation of the likelihood starts.

In this case, each of pixels constituting the perspective image is written to the memory 101 in a predetermined order.

The manager 104 manages the timing to write, to the memory 101, all pixels necessary for calculation of the likelihood in the target pixel in which calculation of the likelihood is first performed by the calculator 102, and starts reading of the perspective image after that timing.

For example, in a case of the perspective image 118, the manager 104 can manage which pixel values in the perspective image 118 have been received so far based on a clock number after the reception of the timing signal 131. Thus, the timing to write, to the memory, all pixels necessary for calculation of the likelihood in the target pixel in which calculation of the likelihood is to be first performed by the calculator 102 can be managed based on the clock number after the reception of the timing signal 131.

Figure 8:
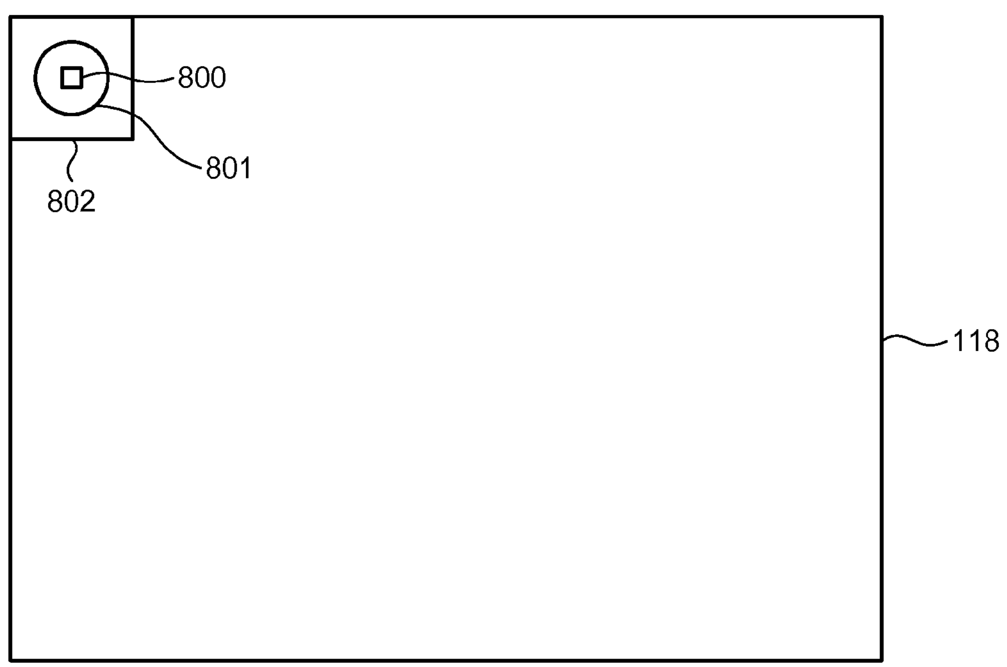
FIG. 8 is an illustrative diagram of an example of a timing management method according to a tenth modification.

FIG. 8 is an illustrative diagram of an example of a timing management method according to the tenth modification. In the example illustrated in FIG. 8, each of pixels of the perspective image 118 is written to the memory 101 starting from the upper left in a raster scan order. In the example illustrated in FIG. 8, calculation of the likelihood is first performed by the calculator 102 in a target pixel 800. All pixels necessary for calculation of the likelihood in the target pixel 800 are first pixels constituting a first region 801 and second pixels constituting a second region 802.

Therefore, the manager 104 manages the timing when all of the first pixels and the second pixels are written to the memory 101, based on the clock number after the reception of the timing signal 131, to manage the timing to write, to the memory 101, all of the pixels necessary for the calculation of the likelihood in the target pixel 800.

Then, once the perspective image is read after that timing, the calculator 102 starts calculation of the likelihood for each target pixel.

According to the tenth modification, since a time of starting the calculation of the likelihood can be put ahead, a time of completing the calculation of the likelihood can also be put ahead. Thus, the likelihood calculation time can be shortened. As a result, a possibility of completing likelihood calculation by the time when treatment beams are to be emitted can be increased. Accordingly, a state in which the completion of likelihood calculation and the irradiation with treatment beams cannot be achieved can be inhibited. Furthermore, the frequency of the generation (imaging) of the perspective image can be reduced, enabling decrease in the exposure dose of the subject by perspective radiation. Furthermore, a time from the generation (imaging) of the perspective image to the irradiation with treatment beams can be shortened.

Eleventh Modification

In the above-mentioned embodiment, all pixels of the perspective image are written to the memory 101. Alternatively, pixels necessary for calculation of the likelihood may be written to the memory 101.

According to an eleventh modification, a time of transferring the perspective image can be shortened. As a result, a possibility of completing likelihood calculation by the time when treatment beams are to be emitted can be increased. Accordingly, a state in which the completion of likelihood calculation and the irradiation with treatment beams cannot be achieved can be inhibited. Furthermore, the frequency of the generation (imaging) of the perspective image can be reduced, enabling decrease in the exposure dose of the subject by perspective radiation. Also, a time from the generation (imaging) of a perspective image to the irradiation with treatment beams can be shortened.

The higher the frame rate of the perspective image is, the more effective the method according to the eleventh modification is.

Twelfth Modification

In the above-mentioned embodiment, the perspective image is an image of all color components. Alternatively, the perspective image may be an image of a color component corresponding to the transmittance of the object.

For example, when the radiation detectors 116 and 117 are implemented by a combination of a color image intensifier and a camera that photographs a Bayer RAW image using a Bayer-type color filter, the perspective images 118 and 119 may be formed with a specific color component of the Bayer RAW image.

In the combination of a color image intensifier and a Bayer-type camera, an R (red) component has highest sensitivity to a low transmittance object, and a B (blue) component has highest sensitivity to a high transmittance object. Therefore, when the object is a marker having a low transmittance, the perspective images 118 and 119 may be formed with the R (red) component of the Bayer RAW image, and when the object is the affected area in which transmittance is not low, the perspective images 118 and 119 may be formed with a G component or a B component of the Bayer RAW image.

Alternatively, the Bayer RAW image may be subjected to demosaicing so that the perspective images 118 and 119 are formed with a specific color component. It is noted that when demosaicing is not performed, the number of pixels for the color component is small, and therefore a time for image processing can be shortened.

Alternatively, for example, when the radiation detectors 116 and 117 are implemented by a combination of a color image intensifier and a camera that photographs only a specific color component, the perspective images 118 and 119 may be formed with an image of the specific color component.

For example, when the object is the marker having a low transmittance, a camera using a color filter through which the R component transmits may be employed, so that the perspective images 118 and 119 may be formed with an image made up of only the R component. Also, when the object is the affected area in which transmittance is not low, a camera using a color filter through which the G component or the B component transmits may be employed, so that the perspective images 118 and 119 may be formed with an image made up of only the G component or the B component.

An interpolation processing of demosaicing causes the image to be blurred. Therefore, in this case, there can be obtained an image which is less blurred than the image of only the color component of the image obtained by demosaicing the Bayer RAW image.

According to the twelfth modification, a possibility of failing to track the object can be reduced. As a result, since the number of frames in which the image of the object cannot be tracked decreases, the frequency of the generation (imaging) of the perspective image can be reduced, enabling decrease in the exposure dose of the subject by perspective radiation.

Thirteenth Modification

In the above-mentioned embodiment, when the likelihood whose value size satisfies the predetermined condition is not detected, the detector 103 may output a warning signal to the controller 123, and the controller 123 may allow a warning device (not illustrated in FIG. 1) to control to provide warning based on the warning signal.

In this case, a state in which the image of the object cannot be clearly seen in the perspective images 118 and 119 is brought about. Accordingly, there is a possibility that the position of the object is erroneously detected. For example, when a bone having a low transmittance and an object are overlapped with each other on lines of the radiations 114 and 115, a state in which the image of the object comes not to be clearly seen is caused.

According to a thirteenth modification, such a state is warned to a user such as a medical doctor or a radiation technologist. Therefore, the user can be prompted to increase the strength of the radiations 114 and 115 or to change the irradiation directions of the radiations 114 and 115. Thus, such a state can be eliminated in an early stage. As a result, since the number of frames in which the image of the object cannot be tracked decreases, the frequency of the generation (imaging) of the perspective image can be reduced, enabling decrease in the exposure dose of the subject by perspective radiation.

Alternatively, when the likelihood whose value size satisfies the predetermined condition is not detected, the detector 103 may output a control signal for increasing the strength of radiation to the controller 123, and the controller 123 may allow the first irradiation units 112 and 113 to control to increase the strength of radiation based on the control signal.

Thus, the image of the object comes to be clearly seen in any frame of the perspective images 118 and 119. Therefore, a state in which the image of the object cannot be clearly seen can be eliminated in an early stage. As a result, since the number of frames in which the image of the object cannot be tracked decreases, the frequency of the generation (imaging) of the perspective image can be reduced, enabling decrease in the exposure dose of the subject by perspective radiation.

Fourteenth Modification

In the above-mentioned embodiment, the value of the likelihood is generally larger around the image of the object in some cases. Therefore, when the likelihood is high in the vicinity, merging may be performed. Accordingly, a mistake of detecting original one object as a plurality of objects is eliminated.

Fifteenth Modification

In the above-mentioned embodiment, the likelihood whose value is large in a region expected as the object is calculated to detect a portion having a large likelihood as the object. Alternatively, a feature value which is small in a portion expected as the object may be calculated and detects, as the object, a portion having a small feature value. This feature value may be designed to be smaller as the pixel values of the first pixels are closer to each other, and a difference between the pixel values of the first pixels and the pixel values of the second pixels is larger. For example, $\sigma_t^2/\sigma_b^2$ or $\sigma_w^2/\sigma_b^2$ can be used as the characteristic amount.

Hardware Configuration

FIG. 9 is a block diagram illustrating an example of a hardware configuration of a treatment system 1 according to the embodiment and modifications described herein. Although description has been made on an assumption that treatment beams are heavy particle beams in the above, FIG. 9 is a block diagram on an assumption that treatment beams are X-rays. As illustrated in FIG. 9, the treatment system 1 includes a console 10, an imaging device 20, a bed device 30, a treatment planning device 40, and a radiation treatment device (LINAC: a radiation treatment device of irradiating with radiation based on treatment planning data for treatment) 50. Although an example in which the imaging device 20 is a CT device is described, no limitation is made thereto.

The console 10 corresponds to the tracking device 100 and the controller 123; the bed device 30 corresponds to the bed 110; the treatment planning device 40 corresponds to the treatment planning device not illustrated in the drawing in the embodiment described above; and the radiation treatment device 50 corresponds to the second irradiation unit 120.

The imaging device 20, the bed device 30, and the radiation treatment device 50 are usually placed in an examination room. On the other hand, the console 10 is usually placed in a control room neighboring to the examination room. The treatment planning device 40 is placed outside the examination room and the control room. Here, the treatment planning device 40 may be placed in the control room or may be a device integrated with the console 10. Representative examples of the imaging device 20 may include an X-ray CT device, an MRI (magnetic resonance imaging) device, and an X-ray device. Hereinafter, a case in which an X-ray CT device 20*a* is used as the imaging device 20 is described.

The console 10 of the treatment system 1 is, as illustrated in FIG. 9, configured based on a computer, and can mutually communicate with a network such as a LAN (local area network) that is a hospital backbone not illustrated in the drawing. The console 10 is largely constituted by basic hardware such as a CPU 11, a main memory 12, an image memory 13, a HDD (hard disc drive) 14, an input device 15, a display device 16, and a tracking device 100. The display device 16 also functions as the above-described warning device. The CPU 11 is interconnected to each hardware component constituting the console 10, through a bus as a common signal transmission path. Here, the console 10 may be provided with a recording medium drive.

The CPU 11 is a controller having a configuration of an integrated circuit (LSI) in which electronic circuits constituted by semiconductors are sealed in a package having a plurality of terminals. When the input device 15 is operated by an operator such as a medical doctor to input an instruction, the CPU 11 executes a program stored in the main memory 12. Alternatively, the CPU 11 loads, to the main memory 12, a program stored in the HDD 14, a program transferred from a network and installed in the HDD 14, or a program read from a recording medium attached to a recording medium drive (not illustrated in the drawing) and installed in the HDD 14, and then executes the program.

The main memory 12 is a storage device configured so as to additionally include an element such as a ROM (read only memory) and a RAM (random access memory). The main memory 12 stores an IPL (initial program loading), a BIOS (basic input/output system) and data, and is used for temporarily storing work memory and data of the CPU 11.

The image memory 13 is a storage device that stores perspective images, slice data as two-dimensional image data, and treatment planning volume data and immediately-before-treatment volume data as three-dimensional image data.

The HDD 14 is a storage device configured such that a metal disk coated or deposited with a magnetic body is included therein in an undetachable manner. The HDD 14 is a storage device that stores a program (including an OS (operating system) and the like as well as an application program) and data installed in the console 10. Also, the OS may provide a GUI (graphical user interface) that allows for heavy use of graphics for information on the display device 16 displayed to an operator such as a practitioner and for basic operation through the input device 15.

The input device 15 is a pointing device to be operable by an operator. An input signal in accordance with the operation is sent to the CPU 11.

The display device 16 includes an image synthesis circuit which is not illustrated in the diagram, a VRAM (video random access memory), a display and the like. The image synthesis circuit generates synthesis data synthesized from image data and, for example, character data with various parameters. The VRAM develops the synthesis data as display image data to be displayed on a display. The display is constituted by a liquid crystal display, a CRT (cathode ray tube) and the like, and sequentially displays the display image data as a display image.

The console 10 controls operation of the X-ray CT device 20*a*, the bed device 30, and the radiation treatment device 50. Furthermore, the console 10 performs logarithm conversion processing or correction processing (preprocessing) such as sensitivity correction, to raw data input from a DAS 24 of the X-ray CT device 20*a*. Then, the console 10 generates slice data as two-dimensional image data and volume data as three-dimensional image data based on projection data.

The X-ray CT device 20*a* of the treatment system 1 images a region containing a treatment site, in order to display image data of the region containing a treatment site such as an affected area of the subject 111. The X-ray CT device 20*a* is provided with an X-ray tube 21 as a radiation source, a diaphragm 22, an X-ray detector 23, a DAS (data acquisition system) 24, a rotation unit 25, a high voltage supply device 26, a diaphragm drive device 27, a rotation drive device 28, and an imaging controller 29.

The X-ray tube 21 allows electron beams to collide with a metal target in accordance with a tube voltage supplied from the high voltage supply device 26 so as to generate damping X-rays, and then irradiates the X-ray detector 23 with the X-rays. The X-rays emitted from the X-ray tube 21 causes fan beam X-rays or cone beam X-rays to be formed.

The diaphragm 22 adjusts the irradiation range of the X-rays emitted from the X-ray tube 21 by the diaphragm drive device 27. That is, the X-ray irradiation range can be changed by adjusting the opening of the diaphragm 22 by the diaphragm drive device 27.

The X-ray detector 23 is a two-dimensional array type X-ray detector (also called a multi-slice type detector) having a matrix shape, that is, having a plurality of channels in a channel direction and a plurality of arrays of X-ray detection elements in a slice direction. The X-ray detection element of the X-ray detector 23 detects X-rays emitted from the X-ray tube 21.

The DAS 24 amplifies a signal of the transmission data detected by each X-ray detection element of the X-ray detector 23, and converts the amplified signal into a digital signal. The output data from the DAS 24 is supplied to the console 10 through the imaging controller 29.

The rotation unit 25 integrally retains the X-ray tube 21, the diaphragm 22, the X-ray detector 23, and the DAS 24. The rotation unit 25 is configured so as to rotate around the subject 111 integrally with the X-ray tube 21, the diaphragm 22, the X-ray detector 23 and the DAS 24, in a state where the X-ray tube 21 and the X-ray detector 23 are opposed to each other. In this case, a direction parallel to the rotation center axis of the rotation unit 25 is defined as a z-axis direction; and a plane orthogonal to the z-axis direction is defined as an x-axis direction and a y-axis direction.

The high voltage supply device 26 supplies power necessary for irradiation with X-rays, to the X-ray tube 21, under control by the imaging controller 29.

The diaphragm drive device 27 has a mechanism of adjusting the irradiation range in the slice direction of X-rays in the diaphragm 22, under control by the imaging controller 29.

The rotation drive device 28 has a mechanism of rotating the rotation unit 25 so that the rotation unit 25 rotates around a cavity in a state where the positional relationship thereof is maintained, under control by the imaging controller 29.

The imaging controller 29 is constituted by a CPU and a memory. The imaging controller 29 controls the X-ray tube 21, the X-ray detector 23, the DAS 24, the high voltage supply device 26, the diaphragm drive device 27, the rotation drive device 28 and the like, thereby to execute scanning while the bed device 30 is operated.

The bed device 30 of the treatment system 1 includes a top board 31, a top board drive device 32, and a bed controller 39.

The subject 111 can be placed on the top board 31. The top board drive device 32 has a mechanism of moving up and down the top board 31 along the y-axis direction, a mechanism of moving back and forth the top board 31 along the z-axis direction, and a mechanism of rotating the top board 31 around the y-axis direction, under control by the bed controller 39.

The bed controller 39 is constituted by a CPU and a memory. The bed controller 39 controls the top board drive device 32 and the like, thereby to execute scanning while the X-ray CT device 20*a* is operated. Also, the bed controller 39 controls the top board drive device 32 and the like, thereby to execute radiation treatment while the radiation treatment device 50 is operated.

The treatment planning device 40 of the treatment system 1 generates treatment planning data for performing radiation treatment by the radiation treatment device 50, based on the slice data and the volume data imaged with the X-ray CT device 20*a* and generated by the console 10. The radiation treatment device 50 irradiates a medical treatment site of the subject 111 with treatment beams, under control of the console 10 based on the treatment planning data generated by the treatment planning device 40. The treatment planning device 40 is configured based on a computer, and can mutually communicate with a network such as a LAN that is a hospital backbone not illustrated in the drawing. The treatment planning device 40 is largely constituted by basic hardware such as a CPU 41, a main memory 42, a treatment planning memory 43, an HDD 44, an input device 45 and a display device 46. The CPU 41 is interconnected to each hardware component constituting the treatment planning device 40, through a bus as a common signal transmission path. Here, the treatment planning device 40 may be provided with a recording medium drive.

The configuration of the CPU 41 is equivalent to the configuration of the CPU 11 of the console 10. When the input device 45 is operated by an operator to input an instruction, the CPU 41 executes a program stored in the main memory 42. Alternatively, the CPU 41 loads, to the main memory 42, a program stored in the HDD 44, a program transferred from a network and installed in the HDD 44, or a program read from a recording medium attached to a recording medium drive (not illustrated in the drawing) and installed in the HDD 44, and then executes the program.

The configuration of the main memory 42 is equivalent to the configuration of the main memory 12 of the console 10. The main memory 42 stores an IPL, a BIOS and data, and is used for temporarily storing work memory and data of the CPU 41.

The treatment planning memory 43 is a storage device that stores treatment planning data. The configuration of the HDD 44 is equivalent to the configuration of the HDD 14 of the console 10. The configuration of the input device 45 is equivalent to the configuration of the input device 15 of the console 10. The configuration of the display device 46 is equivalent to the configuration of the display device 16 of the console 10.

The treatment planning device 40 calculates the position of the treatment site and the shape of the treatment site for the subject 111 based on the image data generated by the X-ray CT device 20*a*, and determines treatment beams (X-rays, electron beams, neutron beams, proton beams, heavy particle beams or the like) to be emitted to the treatment site, and the energy and irradiation field thereof.

The radiation treatment device 50 of the treatment system 1 can generally generate MV-class radiation. The radiation treatment device 50 is disposed with a diaphragm (collimator) in a radiation generation port section, and the diaphragm achieves the irradiation shape and the dose distribution based on the treatment plan. Recently, there is often used, as the diaphragm, a multi-leaf collimator (MLC) which can form dose distribution corresponding to the complicated tumor shape with a plurality of movable leaves. The radiation treatment device 50 adjusts a radiation irradiation amount by an irradiation field formed by the diaphragm, to extinguish or reduce the treatment site of the subject 111.

The radiation treatment device 50 includes a radiation source 51 as a radiation source, a diaphragm 52, an arm unit 55, a high voltage supply device 56, a diaphragm drive device 57, a rotation drive device 58, and a treatment controller 59.

The radiation source 51 generates radiation in accordance with a tube voltage supplied from the high voltage supply device 56.

The diaphragm 52 adjusts the irradiation range of the radiation emitted from the radiation source 51 by the diaphragm drive device 57. That is, the radiation irradiation range can be changed by adjusting the opening of the diaphragm 52 by the diaphragm drive device 57.

The arm unit 55 integrally retains the radiation source 51 and the diaphragm 52. The arm unit 55 is configured so as to rotate around the subject 111 integrally with the radiation source 51 and the diaphragm 52.

The high voltage supply device 56 supplies power necessary for irradiation with radiation to the radiation source 51 under control by the treatment controller 59.

The diaphragm drive device 57 has a mechanism of adjusting the irradiation range of radiation in the diaphragm 52, under control by the treatment controller 59.

The rotation drive device 58 has a mechanism of rotating the arm unit 55 so as to rotate around a connection portion between the arm unit 55 and a support portion, under control by the treatment controller 59.

The treatment controller 59 is constituted by a CPU and a memory. The treatment controller 59 controls the radiation source 51, the high voltage supply device 56, the diaphragm drive device 57 and the like in accordance with the treatment planning data generated by the treatment planning device 40, thereby to execute irradiation with radiation for treatment while the bed device 30 is operated.

As described above, according to the embodiment and modifications described herein, the exposure dose by perspective radiation can be decreased.

For example, the steps in the flowchart of the above-described embodiment may be changed in an execution order, may be plurally executed in a simultaneous manner, or may be executed in a different order for each implementation, unless the nature of the steps is not impaired.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing device comprising:

a processor; and a memory that stores processor-executable instructions that, when executed by the processor, cause the processor to execute:

acquiring a first perspective image of a subject viewed in a first direction;

setting a first region and a second region on the first perspective image, the first region including a first group of pixels around a target pixel, the second region including a second group of pixels, the second group including a pixel not included in the first group;

calculating a likelihood of a pixel value for the target pixel based on pixel values for pixels included in the first group and the second group, wherein the likelihood increases as a difference between pixel values for pixels included in the first group decreases and a difference between pixel values for pixels included in the first group and the second group increases;

detecting a position of an object in the subject based on the likelihood; and outputting information related to the position which is usable by a controller for controlling irradiation of a treatment beam to the object.

2. The device according to claim 1, wherein the first region has a shape depending on a shape of the object.

3. The device according to claim 2, wherein the acquiring acquires object information regarding a shape and a size of the object, and a projection matrix that is used to project three-dimensional coordinates onto the perspective image;

the calculating calculates a shape and a size of an image of the object appearing on the perspective image using the object information and the projection matrix; and the setting sets the first region with the shape and the size of the image.

4. The device according to claim 1, wherein the likelihood is a correlation ratio between the pixel values for pixels of the first group and the second group.

5. The device according to claim 1, wherein the detecting detects that the position of the object is detected by detecting a target pixel having the likelihood whose value satisfies a predetermined condition.

6. The device according to claim 1, wherein the calculating acquires region information indicating a third region where an image of the object is expected to exist in the perspective image; and calculates, for the target pixel, the likelihood in the third region indicated by the region information.

7. The device according to claim 1, wherein the calculating estimates a third region where an image of the object is expected to exist in the perspective image based on a predetermined motion model; and calculates, for the target pixel, the likelihood in the third region.

8. The device according to claim 7, wherein the detecting sets a prior probability to the third region, a value of the prior probability becoming larger the closer to a position to which the image moves based on the predetermined motion model; and detects a position of the object based on the likelihood and the prior probability of the target pixel.

9. The device according to claim 1, wherein the processor detects a plurality of objects in the subject, the calculating estimates a third region where each of images of the plurality of the objects is expected to exist in the perspective image, based on a predetermined motion model; and calculates the likelihood of the target pixel in each of the plurality of third regions, and the detecting sets a prior probability to the third region where the image is expected to exist for each of the images, a value of the prior probability becoming larger the closer to a position to which the image moves based on the predetermined motion model, a kurtosis of the prior probability distribution being higher when a distance among the plurality of images is not more than a threshold; and detects, for each of the third regions, a position of the object based on the likelihood and the prior probability of the target pixel.

10. The device according to claim 1, further comprising:

a storage to which each pixel constituting the perspective image is written in a predetermined order; and wherein the processor-executable instructions further cause the processor to execute managing a timing to write, to the storage, all pixels necessary for calculation of the likelihood for a target pixel in which calculation of the likelihood is to be first performed, and the calculating starts calculation of the likelihood for the target pixel after passage of the timing.

11. The device according to claim 1, wherein the perspective image is an image of a color component corresponding to a transmittance of the object.

12. The device according to claim 11, wherein when the object is an affected area of the subject, the perspective image is an image of a blue or green component.

13. The device according to claim 11, wherein when the object is a marker indwelled around an affected area of the subject, the perspective image is an image of a red component.

14. The device according to claim 1, wherein the calculating calculates the likelihood for the target pixel in each of a plurality of perspective images perspectively seen an inside of the subject in different directions, and the detecting acquires a projection matrix that is used to project three-dimensional coordinates to the perspective image for each perspective image; detects a target pixel having a likelihood whose value size satisfies a predetermined condition for each perspective image; and detects a three-dimensional position of the object using the projection matrix for each perspective image and the target pixel detected from each perspective image.

15. The device according to claim 14, wherein the processor detects a plurality of objects in the subject, and the detecting acquires region information indicating a third region where each of images of the plurality of objects is expected to exist for each perspective image; detects a plurality of target pixels each having the likelihood whose value satisfies the predetermined condition for each perspective image; detects in which third region each of the plurality of target pixels detected from the perspective image exists, using the region information of the perspective image for each of the perspective images; defines correspondence of the plurality of target pixels detected in each of the plurality of perspective images among the plurality of perspective images; and detects three-dimensional positions of the plurality of objects using the projection matrix for each of the plurality of perspective images and the plurality of target pixels detected from each of the plurality of perspective images and corresponded among the plurality of perspective images.

16. The device according to claim 14, wherein the processor detects a plurality of objects in the subject, and the detecting detects target pixels the likelihood for each of which satisfies the predetermined condition for each perspective image; defines correspondence of the plurality of target pixels detected in each perspective image among the plurality of perspective images by epipolar geometry using the projection matrix for each perspective image; and detects three-dimensional positions of the plurality of objects using the projection matrix for each perspective image and the target pixels detected from each perspective image and corresponded among the perspective images.

17. A treatment system, comprising:

a first irradiator that irradiates a subject with radiation;

a first detector that detects the radiation having passed through the subject, and generates a perspective image seen through an inside of the subject;

a processor; and a memory that stores processor-executable instructions that, when executed by the processor, cause the processor to execute:

acquiring a first perspective image of a subject viewed in a first direction;

setting a first region and a second region on the first perspective image, the first region including a first group of pixels around a target pixel, the second region including a second group of pixels, the second group including a pixel not included in the first group;

calculating a likelihood of a pixel value for the target pixel based on pixel values for pixels included in the first group and the second group, wherein the likelihood increases as a difference between pixel values for pixels included in the first group decreases and a difference between pixel values for pixels included in the first group and the second group increases; and detecting a position of an object in the subject based on the likelihood, wherein the system further comprises a second irradiator configured to irradiate the object with treatment beams, based on the detected position.

18. The system according to claim 17, wherein the processor detects a plurality of objects in the subject, the calculating estimates a third region where each of images of the plurality of objects is expected to exist in the perspective image, based on a predetermined motion model; and calculates the likelihood of the target pixel in each third region, the detector sets a prior probability to the third region where the image is expected to exist for each image, a value of the prior probability becoming larger the closer to a position to which the image moves based on the predetermined motion model; detects, for the third region, a position of the object based on the likelihood and the prior probability of the target pixel; and calculates, when a distance between the plurality of images is not more than a threshold, position information for at least one of the first irradiator and the detector by which the perspective image is generated such that the distance between the plurality of images exceeds the threshold, and the treatment system further comprises a controller that controls a position of at least one of the first irradiator and the detector, based on the position information.

19. The system according to claim 17, further comprising a controller configured to, when the likelihood whose value satisfies a predetermined condition is not calculated, perform at least one of a control to allow a warning device to perform warning or a control to allow the first irradiator to increase a strength of the radiation.

20. A medical image processing method, comprising:

acquiring a first perspective image of a subject viewed in a first direction;

setting a first region and a second region on the first perspective image, the first region including a first group of pixels around a target pixel, the second region including a second group of pixels, the second group including a pixel not included in the first group;

calculating a likelihood of a pixel value for the target pixel based on pixel values for pixels included in the first group and the second group, wherein the likelihood increases as a difference between pixel values for pixels included in the first group decreases and a difference between pixel values for pixels included in the first group and the second group increases;

detecting a position of an object in the subject based on the likelihood; and outputting information related to the position which is usable by a controller for controlling irradiation of a treatment beam to the object.

* * * * *